(12) United States Patent
Moser

(10) Patent No.: US 9,403,780 B2
(45) Date of Patent: *Aug. 2, 2016

(54) PYRIDINE- OR PYRAZINE-CONTAINING COMPOUNDS

(71) Applicant: 3M INNOVATIVE PROPERTIES COMPANY, St. Paul, MN (US)

(72) Inventor: William H. Moser, Edina, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/781,946

(22) PCT Filed: Apr. 23, 2014

(86) PCT No.: PCT/US2014/035132
§ 371 (c)(1),
(2) Date: Oct. 2, 2015

(87) PCT Pub. No.: WO2014/186101
PCT Pub. Date: Nov. 20, 2014

(65) Prior Publication Data
US 2016/0052893 A1    Feb. 25, 2016

Related U.S. Application Data

(60) Provisional application No. 61/822,939, filed on May 14, 2013.

(51) Int. Cl.
*C07D 241/12* (2006.01)
*C07D 213/30* (2006.01)
*C07D 213/40* (2006.01)

(52) U.S. Cl.
CPC ............ *C07D 241/12* (2013.01); *C07D 213/30* (2013.01); *C07D 213/40* (2013.01)

(58) Field of Classification Search
None
See application file for complete search history.

(56) References Cited

U.S. PATENT DOCUMENTS

| 4,122,128 A | 10/1978 | Lehmann |
| 2009/0215785 A1 | 8/2009 | DuBois |

FOREIGN PATENT DOCUMENTS

| KR | 10-2010-0114094 | 10/2010 |
| WO | WO 2014-186151 | 11/2014 |

OTHER PUBLICATIONS

Chen, "Amphiphatic Piperazine, Pyrazine, and Pyridine Derivaties as the Thermal Latency for Epoxy-Phenolic Resins", Polymer Journal, 2009, vol. 41, No. 8, pp. 685-690.
Goto, "Single-Site Modifications and Their Effect on the Folding Stability of m-Phenylene Ethynylene Oligomers", Organic letters. Feb. 2004, vol. 6, No. 6, pp. 889-892.
Jean, "Stereoselective access to heteroarylmethylenesubstituted pyrrolidines: fully organocatalytic Mannich-hydroamination reactions", Chemical Communications, Jan. 2013, vol. 49, pp. 1651-1653.
Nakamura, Bimodal chemiluminescence of 8-chlorostyryl-6-phenylethynylimidazopyrazinone: Large bathochromic shift caused by a styryl group at 8-position, Tetrahedron Letters, 1998. vol. 39, pp. 301-304.
International Search Report for PCT International Application No. PCT/US2014/035132, mailed on Oct. 7, 2014, 6pgs.

*Primary Examiner* — Samantha Shterengarts
(74) *Attorney, Agent, or Firm* — Julie Lapos-Kuchar

(57) ABSTRACT

Described herein are selective bis-alkynyl pyrazines, bis-alkynyl pyridines, bispyridine substituted ellagic acid derivatives, and pyridine-substituted coumarin derivatives and methods of making thereof.

1 Claim, No Drawings

PYRIDINE- OR PYRAZINE-CONTAINING COMPOUNDS

CROSS REFERENCE TO RELATED APPLICATIONS

This application is a national stage filing under 35 U.S.C. 371 of PCT/US2014/035132, filed Apr. 23, 2014, which claims priority to U.S. Application No. 61/822,939, filed May 14, 2013, the disclosure of which is incorporated by reference in its/their entirety herein.

TECHNICAL FIELD

Pyridine- or pyrazine-containing compounds are described along with their methods of making.

SUMMARY

Pyridine- and pyrazine-containing compounds are valued materials in the fields of organic synthesis, supramolecular chemistry, and materials science. The presence of the nitrogen atoms, with their accompanying lone pair of electrons, renders pyridines and pyrazines both basic and nucleophilic, and thus can be used as highly soluble bases or catalysts in a variety of organic transformations. Pyridines and pyrazines are also valuable as synthons in organic synthesis, and are particularly useful in the preparation of pharmaceuticals and agrochemicals due to their propensity towards high biological activity. Pyridines and pyrazines also serve as ligands in the chelation of a variety of metals and metal ions, and the resultant organometallic complexes of pyridines and pyrazines are utilized, for example, as catalysts in asymmetric organic transformations, as dye sensitizers in solar cells, in organic light emitting diodes, and in the fields of artificial photosynthesis and related photogenerated energy transfer processes. Pyridines and pyrazines are also utilized industrially as components of adhesives, films, or other polymeric materials in which their properties, either alone or as metal complexes, impart valuable characteristics to the bulk material. Due to this widespread utility, there is a continuous desire to identify novel pyridine- and/or pyrazine-containing compounds.

In one aspect, pyridine- and pyrazine-containing compounds and their method of making are described, such compounds include those selected from the group consisting essentially of:

(a) bis-alkynyl pyrazine and bis-alkynyl pyridines of the formulas:

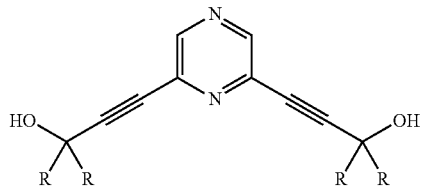

(I)

wherein R is selected from H, CH$_3$, or the two adjacent R groups join to form a cyclohexane ring;

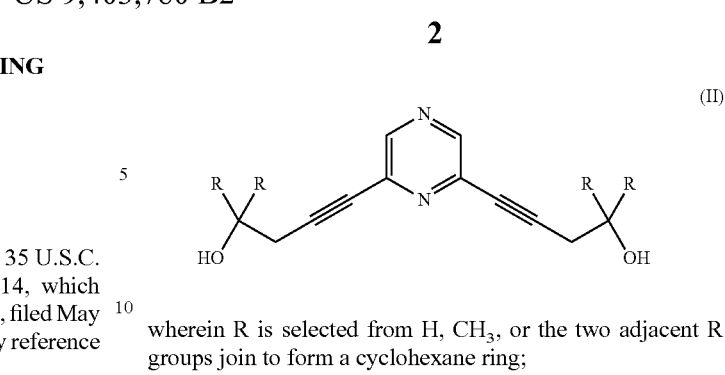

wherein R is selected from H, CH$_3$, or the two adjacent R groups join to form a cyclohexane ring;

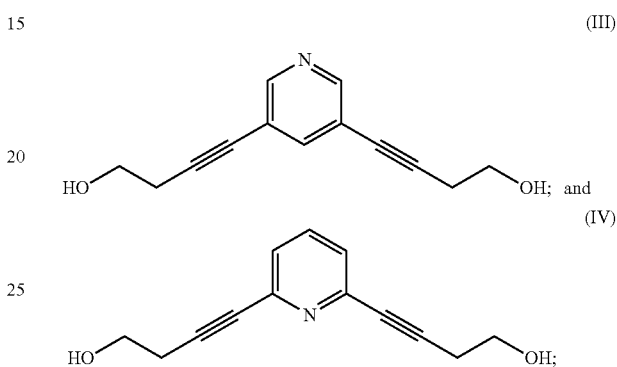

(b) bispyridine substituted ellagic acid derivatives of the formulas:

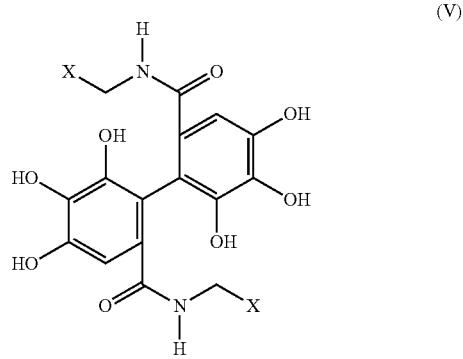

wherein X is a pyridyl group;

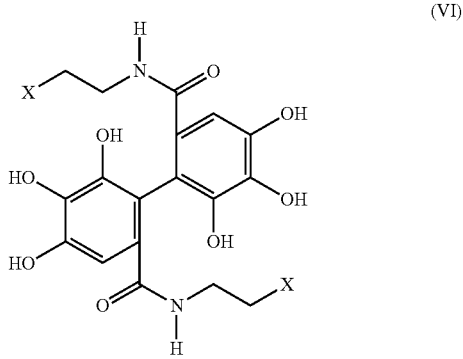

wherein X is a pyridyl group; and

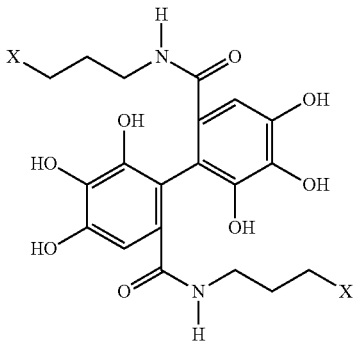

(VII)

wherein X is selected from a pyridyl group; and (c) pyridine-substituted coumarin derivatives of the formulas:

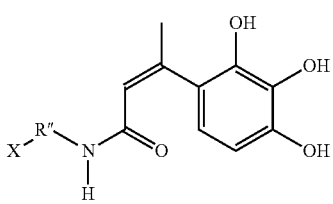

(VIII)

wherein (i) X is a 4-pyridyl group and R" is methylene, ethylene, or a propylene, or (ii) X is a 3-pyridyl group and R" is a methylene;

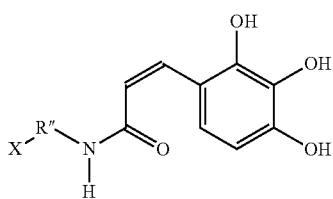

(IX)

wherein X is a 4-pyridyl group and R" is ethylene; and

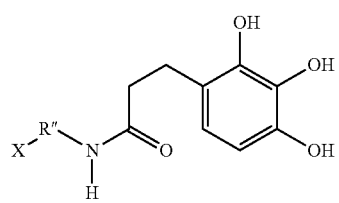

(X)

wherein X is a 4-pyridyl group and R" is ethylene.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and "and/or" is used to indicate one or both stated cases may occur, for example A and/or B includes, (A and B) and (A or B).

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

In the present disclosure three groups of compounds comprising either a pyridine- or pyrazine ring are disclosed based on their method of making. These groups are divided into (a) bis-alkynyl pyrazine and bis-alkynyl pyridines; (b) bispyridine substituted ellagic acid derivatives; and (c) pyridine-substituted coumarin derivatives.

Bis-alkynyl Pyrazine and Bis-alkynyl Pyridines

In the present disclosure, compounds comprising two alkynyl groups (i.e., a triple bond between two carbon atoms) as well as a pyridine or pyrazine group may be prepared from a bis-chloro precursor as shown in the reaction below:

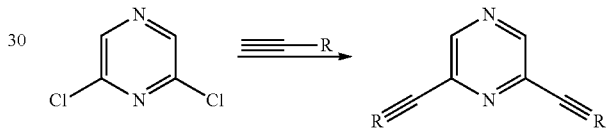

In the above reaction, the bis-chloro precursor is reacted with an alkynyl-terminated compound in the presence of a catalyst under basic conditions in a reaction known as the Sonogashira reaction.

In the present disclosure the bis-chloro precursor may be selected from 2,6-dichloropyrazine, 2,6-dichloropyridine, or 3,5-dichloropyridine.

In the present disclosure, the alkynyl-terminated compound may be selected from: alkynyl-terminated alcohols, comprising 2-10 carbon atoms, including for example, propargyl alcohol; 2-methyl-3-buyn-2-ol, 1-ethynyl-1-cyclohexanol, 3-butyn-1-ol.

The ratio of the alkynyl-terminated compound to the bis-chloro precursor to produce the bis-alkynyl pyrazine or bis-alkynyl pyridine should be at least 2:1 or even 3:1. Preferably there is an excess of alkynyl-terminated compound in the Sonogashira coupling reaction.

The reaction described above is run under basic pH conditions by adding an excess of a base. Exemplary bases include triethylamine, diisopropylamine, N,N-diisopropylethylamine, and cesium carbonate.

The reaction is also run in the presence of one or more catalysts. Such catalysts include palladium and copper. Exemplary palladium catalysts include: bis(triphenylphosphine)palladium (II) dichloride, 1,1'-bis(diphenylphosphino) ferrocene palladium (II) dichloride, and tetrakis(triphenylphosphine)palladium (0). Exemplary copper catalysts include copper (I) iodide. In one embodiment, one catalyst is used; in another embodiment, more than one catalyst is used. Typically the catalysts are added in small quantities such as no more than 5 mol %, 2.5 mol %, 1 mol %, or even 0.5 mol %.

To facilitate the reaction, a solvent is used, typically a polar aprotic solvent system, however polar protics solvents have also been used. Exemplary solvents include: tetrahydrofuran, diethyl ether, methyl tert-butyl ether, dimethylformamide, and acetonitrile.

In one embodiment, the reaction between the bis-chloro precursor and the alkynyl-terminated compound may be conducted at a temperature of between at least room temperature, 25, 30, or even 35° C.; at most 90, 100, or even 150° C.

Final reaction products must be separated from remaining catalysts, catalyst by-products, bases, and other salts present. Such techniques are known in the art. Typically this accomplished by filtration of the reaction mixture through a stationary phase such as diatomaceous earth (Celite) and/or washing the reaction mixture with an aqueous phase. Upon removal of the solvent and/or other volatile components under reduced pressure, the reaction product can optionally be purified by silica gel chromatography and/or crystallization from an appropriate solvent.

Exemplary compounds made according to the above reaction include:

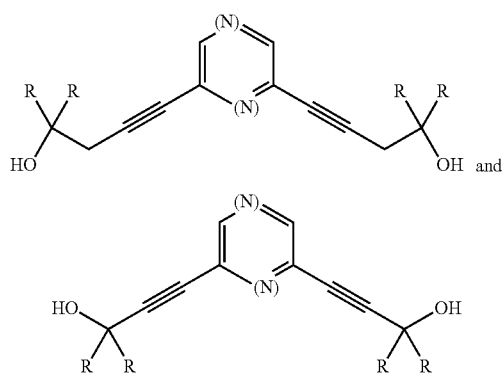

wherein R is selected from H or a C1-C4 alkyl group or the two adjacent R groups join to form a cyclohexane ring and the aromatic ring comprises 1 or 2 nitrogen atoms. Specific pyrazine-containing compounds include for example:

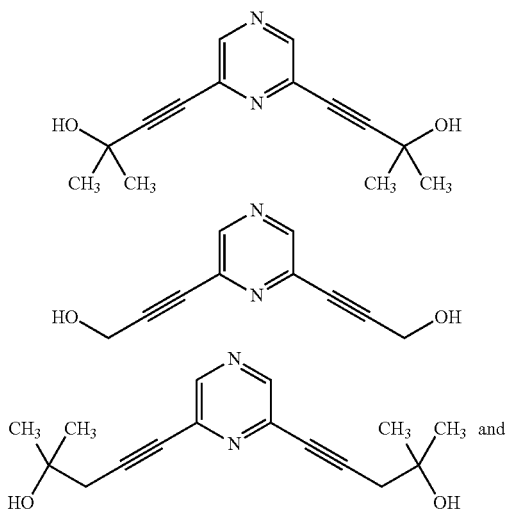

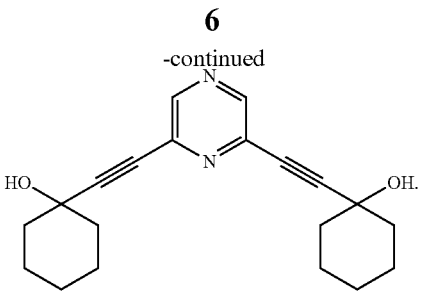

Specific pyridine-containing compounds include:

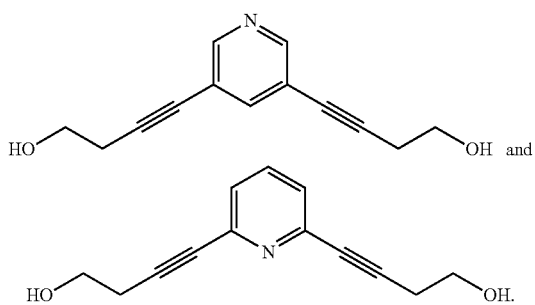

Bispyridine Substituted Ellagic Acid Derivatives

In the present disclosure, compounds comprising two pyridine groups (i.e., C5H5N) are prepared from Ellagic acid as shown in the reaction below:

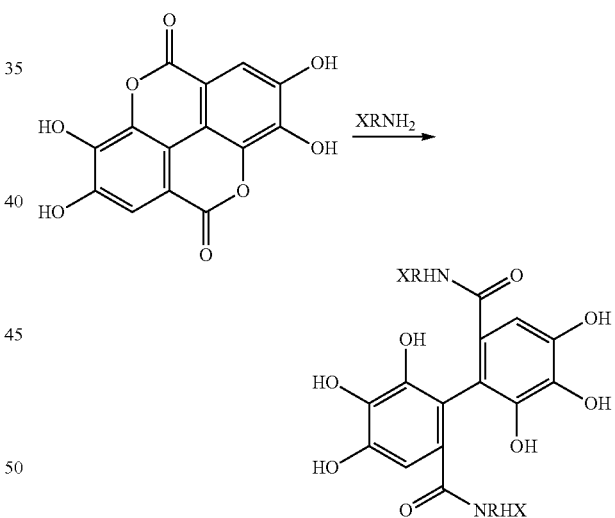

In the above reaction, Ellagic acid is reacted with a primary amine-substituted pyridine compound ($XRNH_2$) to form bispyridine derivatives.

In the present disclosure, Ellagic acid may be used and/or alternatively a salt or hydrate form of Ellagic acid.

As used herein, $XRNH_2$ represents a primary amine-substituted pyridine compound, wherein R is a bond, or a C1-C4 alkylene group. The pyridine may be a 2-, 3-, or 4-pyridyl group. Exemplary primary amine-substituted pyridine compounds include: 2-(aminomethyl)pyridine, 3-(aminomethyl)pyridine, 4-(aminomethyl)pyridine, 2-(2-aminoethyl)pyridine, 3-(2-aminoethyl)pyridine, 4-(2-aminoethyl)pyridine, 3-(2-pyridyl)-1-propanamine, 3-(3-pyridyl)-1-propanamine, and 3-(4-pyridyl)-1-propanamine.

The ratio of the primary amine-substituted pyridine compound to the Ellagic acid to produce the bispyridine substituted ellagic acid derivative is at least 2:1 or even 3:1. Preferably there is an excess of the primary amine-substituted pyridine compound in the addition reaction.

To facilitate the reaction, a solvent is used, specifically a polar aprotic solvent system. Exemplary solvents include: tetrahydrofuran, methyl tert-butyl ether, dimethylformamide, and acetonitrile.

In one embodiment, the reaction between the primary amine-substituted pyridine compound and the Ellagic acid is conducted at temperatures higher than room temperature. Typically at the reflux temperature of the solvent is used, for example, temperatures between at least room temperature, 25, 30, or even 35° C.; at most 90, 100, or 150° C.

To facilitate the reaction, in one embodiment, a catalyst may be added. The catalyst may increase the rate of reaction at any given temperature, or allow the reaction to be performed at a lower temperature. Exemplary catalysts include 4-dimethylaminopyridine and 1,4-diazabicyclo[2.2.2]octane. Amounts of catalysts added may be no more than 10 mol %, 5 mol %, or even 2 mol %.

In one embodiment, the resulting product may be collected via filtration and washed with solvent.

Exemplary compounds made according to the above reaction include:

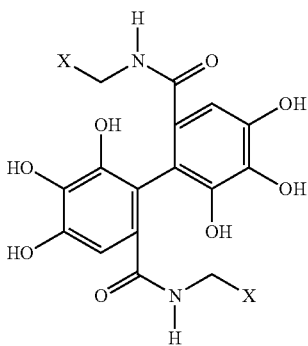

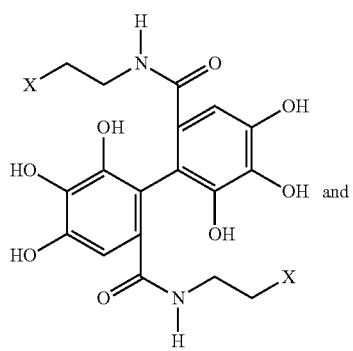

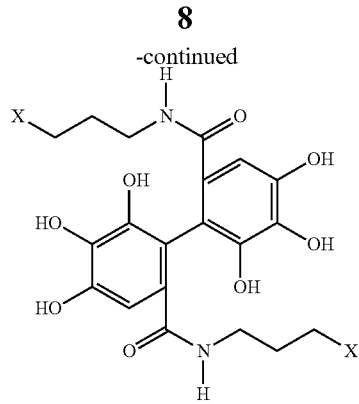

wherein X is selected from a pyridyl group (2-, 3-, or 4-pyridyl group).

Pyridine-Substituted Coumarin Derivatives

In the present disclosure, compounds comprising a pyridine group (i.e., C5H5N) are prepared from a coumarin ring opening reaction as shown in the reaction below:

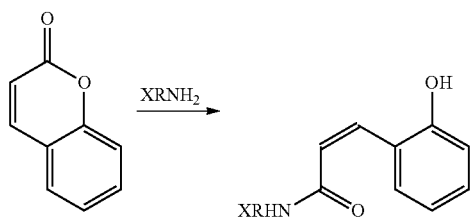

In the above reaction, a coumarin is reacted with a primary amine-substituted pyridine compounds to form a pyridine-substituted coumarin derivative.

Coumarin starting materials include: 4-methylesculetin, coumarin, dihydrocoumarin, and 7,8-dihydroxy-4-methylcoumarin.

As used herein, XRNH$_2$ represents a primary amine-substituted pyridine compound, wherein R is a bond, or a C1-C4 alkylene group. In the present disclosure, the primary amine-substituted pyridine compounds may be selected from: 2-(aminomethyl)pyridine, 3-(aminomethyl)pyridine, 4-(aminomethyl)pyridine, 2-(2-aminoethyl)pyridine, 3-(2-aminoethyl)pyridine, 4-(2-aminoethyl)pyridine, 3-(2-pyridyl)-1-propanamine, 3-(3-pyridyl)-1-propanamine, and 3-(4-pyridyl)-1-propanamine.

The ratio of the primary amine-substituted pyridine compound to the coumarin to produce the pyridine substituted coumarin derivative should be at least 1:1 or even 1.5:1. Preferably there is an excess of the primary amine-substituted pyridine compound in the addition reaction.

To facilitate the reaction, a solvent is used, specifically a polar aprotic solvent system. Exemplary solvents include: tetrahydrofuran, methyl tert-butyl ether, dimethylformamide, and acetonitrile.

In one embodiment, the reaction between the primary amine-substituted pyridine compound and the coumarin is conducted at temperatures higher than room temperature. Typically at the reflux temperature of the solvent used, for example, temperatures between at least room temperature, 25, 30, or even 35° C.; at most 90, 100, or 150° C.

To facilitate the reaction, a catalyst may be added. The catalyst may increase the rate of reaction at any given temperature, or allow the reaction to be performed at a lower temperature. Exemplary catalysts include 4-dimethylaminopyridine and 1,4-diazabicyclo[2.2.2]octane. Amounts of catalysts added may be no more than 10 mol %, 5 mol %, or even 2 mol %.

Exemplary compounds made according to the above reaction include:

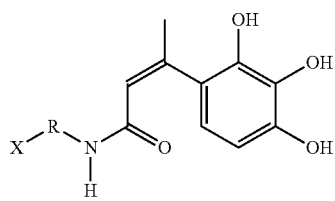

wherein (i) X is a 4-pyridyl group and R is methylene, ethylene, or a propylene, or (ii) X is a 3-pyridyl group and R is a methylene;

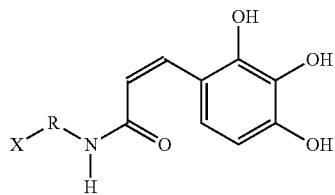

wherein X is a 4-pyridyl group and R is ethylene; and

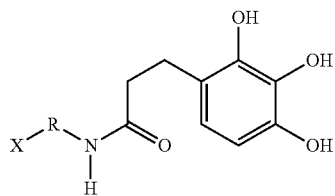

wherein X is a 4-pyridyl group and R is ethylene.

In one embodiment, the compounds as disclosed herein may be used as starting materials, or may be used in compositions such as epoxy adhesives and epoxy powder coatings as disclosed in U.S. Appl. No. 61/823,111, filed May 14, 2013, the disclosure herein incorporated by reference in its entirety.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, kg=kilograms, min=minutes, mol=mole; cm=centimeter, mm=millimeter, ml=milliliter, L=liter, psi=pressure per square inch, MPa=megaPascals, and wt=weight.

| Materials | |
|---|---|
| Material | Source |
| Acetonitrile | EMD Chemicals, Inc.; Gibbstown, NJ |
| 4-Acetylpyridine | Sigma Aldrich; St. Louis, MO |
| 4-(2-Aminoethyl)pyridine | TCI America; Portland, OR |
| Aminoguanidine sulfate | Alfa Aesar; Ward Hil, MA |
| Bis(triphenylphosphine) palladium(II) dichloride | TCI America; Portland, OR |
| 3-Butyn-1-ol | Sigma Aldrich; St. Louis, MO |
| Copper (I) iodide | Sigma Aldrich; St. Louis, MO |
| Dichloromethane | EMD Chemicals, Inc.; Gibbstown, NJ |
| 2,6-Dichloropyrazine | Sigma Aldrich; St. Louis, MO |
| 7,8-Dihydroxy-4-methylcoumarin | Sigma Aldrich; St. Louis, MO |
| Ellagic acid | AmplaChem, Inc.; Carmel, IN |
| Ethyl acetate | EMD Chemicals, Inc.; Gibbstown, NJ |
| Hexane | EMD Chemicals, Inc.; Gibbstown, NJ |
| Silica gel (230-400 Mesh) | Alfa Aesar; Ward Hil, MA |
| Tetrahydrofuran | EMD Chemicals, Inc.; Gibbstown, NJ |
| Triethylamine | EMD Chemicals, Inc.; Gibbstown, NJ |

NMR: Nuclear magnetic resonance spectra (proton - 1H NMR) were analyzed and recorded using an NMR spectrometer (UltraShield ™Plus 500 MHz NMR spectrometer; Bruker Corporation; Billerica, MA).

Preparation of Bis-alkynyl pyrazine

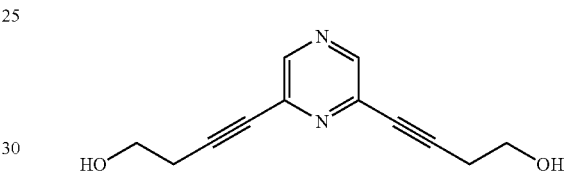

A 500 mL three neck round-bottomed flask was equipped with a reflux condenser, pressure-equalizing addition funnel, and magnetic stirbar. 2,6-dichloropyrazine (14.0 g, 94.0 mmol), 3-butyn-1-ol (16.5 g, 235 mmol), triethylamine (39.4 mL, 282 mmol), and 200 mL acetonitrile were added to the flask, and the resultant solution was degassed using several cycles of evacuation/nitrogen back flow. Copper iodide (1.80 g, 9.40 mmol) and bis(triphenylphosphine) palladium(II) dichloride (1.65 g, 2.35 mmol) were added to the solution, and the degassing procedure was repeated. The reaction mixture was heated at reflux overnight under nitrogen atmosphere with vigorous stirring. Silica gel was added to the reaction mixture, and the volatile components were evaporated under reduced pressure. The adsorbed material was loaded onto a silica gel filter column and eluted with ethyl acetate to afford the product (11.6 g, 57% of theoretical yield) as a yellow solid. 1H NMR (500 MHz, CDCl$_3$): δ 8.51 (s, 2H), 3.91 (q, J=6.4 Hz, 4H), 3.56 (t, J=6.4 Hz, 2H), 2.77 (t, J=6.4 Hz, 2H).

Preparation of Ellagic Acid Adduct

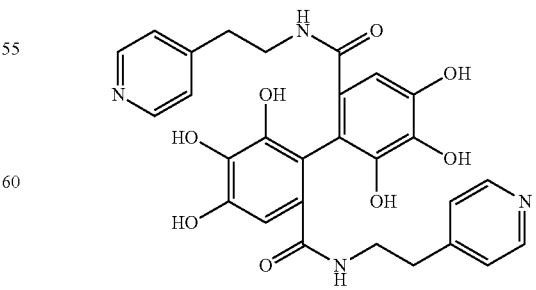

To a 250 mL round-bottomed flask equipped with magnetic stirbar was added ellagic acid (9.07 g, 30.0 mmol) and tetrahydrofuran (40 mL). A solution of 4-(2-aminoethyl)pyridine (7.33 g, 60.0 mmol) in tetrahydrofuran (20 mL) was added via pipette, and the resultant mixture was heated at reflux overnight while stirring vigorously. After cooling to ambient temperature, the precipitated product was collected via filtration, washing with additional tetrahydrofuran. Drying under vacuum provided the product (13.5 g, 83% of theoretical yield) as a tan solid. 1H NMR (500 MHz, $d_6$-DMSO): δ 8.50 (d, J=5.8 Hz, 4H), 7.29 (d, J=5.8 Hz, 4H), 7.20 (s, 2H), 3.07 (m, 4H), 2.84 (m, 4H).

Preparation of Coumarin Derivative

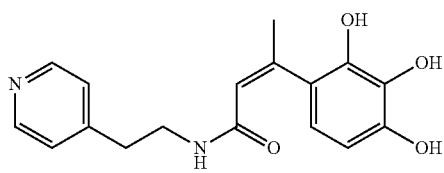 [SMILES: C/C(=C/C(=O)NCCc1ccncc1)c1ccc(O)c(O)c1O]

To a 250 mL round-bottomed flask equipped with magnetic stirbar was added 7,8-dihydroxy-4-methyl coumarin (3.64 g, 20.0 mmol) and tetrahydrofuran (30 mL). A solution of 4-(2-aminoethyl)pyridine (2.44 g, 20.0 mmol) in tetrahydrofuran (20 mL) was added via pipette, and the resultant mixture was heated at reflux overnight while stirring vigorously. The majority of the tetrahydrofuran was evaporated under reduced pressure to afford a thick orange oil. A 1:1 Ethyl acetate/dichloromethane solution (100 mL) was added, and the resultant mixture was heated at reflux while stirring vigorously. The yellow precipitate which formed was collected via filtration and dried under vacuum to afford the product (4.56 g, 75% of theoretical yield). 1H NMR (500 MHz, $d_6$-DMSO): δ 8.46 (dd, J1=1.6 Hz, J2=4.4 Hz, 2H), 7.25 (dd, J1=1.6 Hz, J2=4.4 Hz, 2H), 7.05 (d, J=8.6 Hz, 1H), 6.77 (d, J=8.6 Hz, 1H), 6.07 (d, J=1.0 Hz, 1H), 2.87 (t, J=7.4 Hz, 2H), 2.72 (t, J=7.4 Hz, 2H), 2.35 (d, J=1.0 Hz, 3H).

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A compound selected from the group consisting of:
   (a) a bis-alkynyl pyrazine or a bis-alkynyl pyridine of the formula:

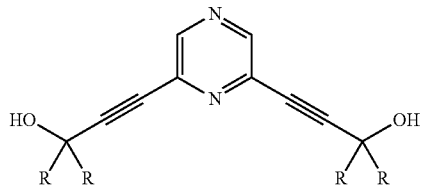

(I)

wherein R is selected from H, CH₃, or the two adjacent R groups join to form a cyclohexane ring;

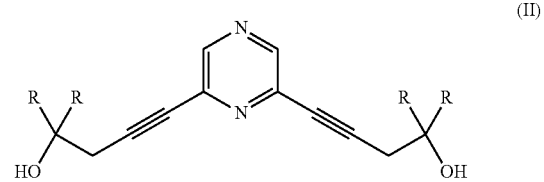

(II)

wherein R is selected from H, CH₃, or the two adjacent R groups join to form a cyclohexane ring;

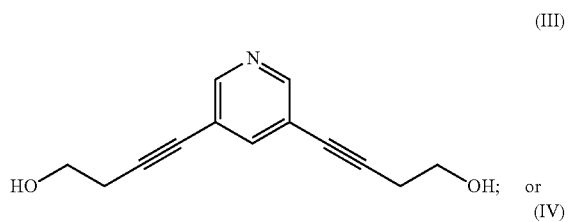

(III)

or (IV)

(b) a bispyridine substituted ellagic acid derivative of the formula:

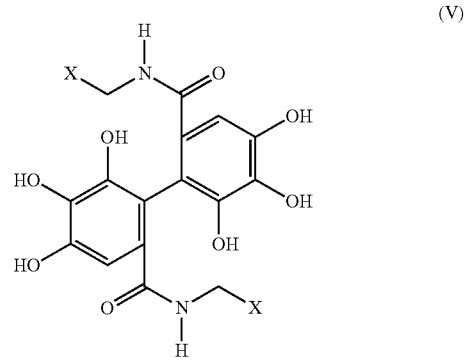

(V)

wherein X is a pyridyl group;

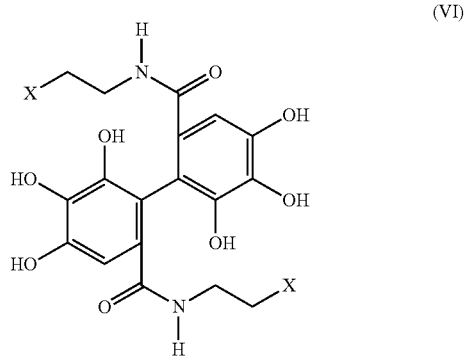

(VI)

wherein X is a pyridyl group; or
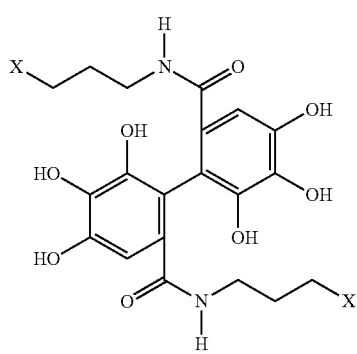
(VII)
wherein X is a pyridyl group; and
(c) a pyridine-substituted coumarin derivative of the formula:
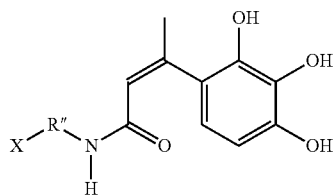
(VIII)
wherein (i) X is a 4-pyridyl group and R" is methylene, ethylene, or a propylene, or (ii) X is a 3-pyridyl group and R" is a methylene;
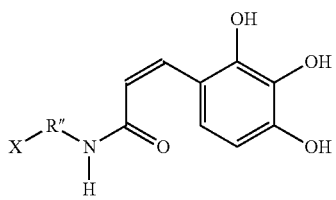
(IX)
wherein X is a 4-pyridyl group and R" is ethylene; or
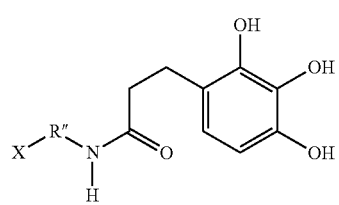
(X)
wherein X is a 4-pyridyl group and R" is ethylene.
* * * * *